(12) United States Patent
Kirschman

(10) Patent No.: US 7,963,982 B2
(45) Date of Patent: Jun. 21, 2011

(54) IMPLANT PLATE SCREW LOCKING SYSTEM AND SCREW HAVING A LOCKING MEMBER

(75) Inventor: David Louis Kirschman, Dayton, OH (US)

(73) Assignee: X-spine Systems, Inc., Maimisburg, OH (US)

( * ) Notice: Subject to any disclaimer, the term of this patent is extended or adjusted under 35 U.S.C. 154(b) by 959 days.

(21) Appl. No.: 11/778,284

(22) Filed: Jul. 16, 2007

(65) Prior Publication Data

US 2009/0024170 A1    Jan. 22, 2009

(51) Int. Cl.
*A61B 17/86* (2006.01)

(52) U.S. Cl. ........................................ 606/305; 606/291

(58) Field of Classification Search .................. 606/280, 606/281, 289, 291, 305, 69, 250, 287, 288; 411/114, 115, 161–163, 299, 326, 329
See application file for complete search history.

(56) References Cited

U.S. PATENT DOCUMENTS

| | | | |
|---|---|---|---|
| 1,025,008 | A | 4/1912 | Miner |
| 2,677,369 | A | 5/1954 | Knowles |
| 3,848,601 | A | 11/1974 | Ma et al. |
| 3,867,728 | A | 2/1975 | Stubstad et al. |
| 4,157,715 | A | 6/1979 | Westerhoff |
| 4,309,777 | A | 1/1982 | Patil |
| 4,349,921 | A | 9/1982 | Kuntz |
| 4,488,543 | A | 12/1984 | Tornier |
| 4,553,273 | A | 11/1985 | Wu |
| 4,599,086 | A | 7/1986 | Doty |
| 4,611,581 | A | 9/1986 | Steffee |

(Continued)

FOREIGN PATENT DOCUMENTS

CA        1292596        12/1991
(Continued)

*Primary Examiner* — Eduardo C Robert
*Assistant Examiner* — Christian Sevilla
(74) *Attorney, Agent, or Firm* — Jacox, Meckstroth & Jenkins

(57) ABSTRACT

Spinal fusion system and method utilizing an implant and screw, wherein at least one pawl is mounted on or integral with the screw to prevent said plate or screw from moving in at least one of an axial direction or a rotational direction.

25 Claims, 7 Drawing Sheets

U.S. PATENT DOCUMENTS

| | | | |
|---|---|---|---|
| 4,696,290 | A | 9/1987 | Steffee |
| 4,714,469 | A | 12/1987 | Kenna |
| 4,743,256 | A | 5/1988 | Brantigan |
| 4,759,766 | A | 7/1988 | Buettner-Janz et al. |
| 4,834,757 | A | 5/1989 | Brantigan |
| 4,878,915 | A | 11/1989 | Brantigan |
| 4,988,349 | A | 1/1991 | Pennig |
| 4,997,432 | A | 3/1991 | Keller |
| 5,041,113 | A | 8/1991 | Biedermann et al. |
| 5,084,049 | A | 1/1992 | Asher et al. |
| 5,085,660 | A | 2/1992 | Lin |
| 5,192,327 | A | 3/1993 | Brantigan |
| 5,246,443 | A | 9/1993 | Mai |
| 5,261,911 | A | 11/1993 | Carl |
| 5,267,423 | A | 12/1993 | Giannuzzi |
| 5,275,601 | A * | 1/1994 | Gogolewski et al. ......... 606/291 |
| 5,290,312 | A | 3/1994 | Kojimoto et al. |
| 5,324,290 | A | 6/1994 | Zdeblick et al. |
| 5,330,473 | A | 7/1994 | Howland |
| 5,364,399 | A | 11/1994 | Lowery et al. |
| 5,405,391 | A | 4/1995 | Hednerson et al. |
| 5,425,772 | A | 6/1995 | Brantigan |
| 5,439,463 | A | 8/1995 | Lin |
| 5,549,612 | A | 8/1996 | Yapp et al. |
| 5,554,191 | A | 9/1996 | Lahille et al. |
| 5,601,551 | A | 2/1997 | Taylor et al. |
| 5,601,553 | A | 2/1997 | Trebing et al. |
| 5,616,142 | A | 4/1997 | Yuan et al. |
| 5,616,144 | A | 4/1997 | Yapp et al. |
| 5,620,443 | A | 4/1997 | Gertzbein et al. |
| 5,672,177 | A | 9/1997 | Seldin |
| 5,681,310 | A | 10/1997 | Yuan et al. |
| 5,681,311 | A | 10/1997 | Foley et al. |
| 5,702,395 | A | 12/1997 | Hopf |
| 5,713,899 | A | 2/1998 | Marnay et al. |
| 5,713,900 | A | 2/1998 | Benzel et al. |
| 5,716,415 | A | 2/1998 | Steffee |
| 5,720,746 | A | 2/1998 | Soubeiran |
| 5,776,196 | A | 7/1998 | Matsuzaki et al. |
| 5,843,082 | A | 12/1998 | Yuan et al. |
| 5,876,402 | A | 3/1999 | Errico et al. |
| 5,888,228 | A | 3/1999 | Knothe et al. |
| 5,904,683 | A | 5/1999 | Pohndorf et al. |
| 5,925,047 | A | 7/1999 | Errico et al. |
| 5,951,558 | A | 9/1999 | Fiz |
| 5,954,722 | A | 9/1999 | Bono |
| 6,030,389 | A | 2/2000 | Wagner et al. |
| 6,066,175 | A | 5/2000 | Henderson et al. |
| 6,106,557 | A | 8/2000 | Robioneck et al. |
| 6,136,002 | A | 10/2000 | Shih et al. |
| 6,139,550 | A | 10/2000 | Michelson |
| 6,152,927 | A | 11/2000 | Farris et al. |
| 6,159,211 | A | 12/2000 | Boriani et al. |
| 6,159,213 | A | 12/2000 | Rogozinski |
| 6,159,245 | A | 12/2000 | Meriwether et al. |
| 6,171,307 | B1 | 1/2001 | Orlich |
| 6,193,721 | B1 | 2/2001 | Michelson |
| D440,311 | S | 4/2001 | Michelson |
| 6,224,602 | B1 | 5/2001 | Hayes |
| 6,235,033 | B1 | 5/2001 | Brace et al. |
| 6,235,034 | B1 | 5/2001 | Bray |
| 6,235,059 | B1 | 5/2001 | Benezech et al. |
| 6,245,108 | B1 | 6/2001 | Biscup |
| 6,258,089 | B1 | 7/2001 | Campbell et al. |
| 6,261,291 | B1 | 7/2001 | Talaber et al. |
| 6,261,586 | B1 | 7/2001 | McKay |
| 6,264,655 | B1 | 7/2001 | Pisharodi |
| 6,293,949 | B1 | 9/2001 | Justis et al. |
| D449,692 | S | 10/2001 | Michelson |
| 6,306,136 | B1 | 10/2001 | Baccelli |
| 6,306,139 | B1 | 10/2001 | Fuentes |
| 6,328,738 | B1 | 12/2001 | Suddaby |
| 6,361,537 | B1 | 3/2002 | Anderson |
| 6,368,351 | B1 | 4/2002 | Glenn et al. |
| 6,383,186 | B1 | 5/2002 | Michelson |
| 6,398,783 | B1 | 6/2002 | Michelson |
| 6,413,259 | B1 | 7/2002 | Lyons et al. |
| 6,416,528 | B1 | 7/2002 | Michelson |
| 6,428,542 | B1 | 8/2002 | Michelson |
| 6,432,106 | B1 | 8/2002 | Fraser |
| 6,454,769 | B2 | 9/2002 | Wagner et al. |
| 6,454,771 | B1 | 9/2002 | Michelson |
| 6,485,517 | B1 | 11/2002 | Michelson |
| 6,503,250 | B2 | 1/2003 | Paul |
| 6,527,776 | B1 | 3/2003 | Michelson |
| 6,533,786 | B1 | 3/2003 | Needham et al. |
| 6,558,423 | B1 | 5/2003 | Michelson |
| 6,558,424 | B2 | 5/2003 | Thalgott |
| 6,569,201 | B2 | 5/2003 | Moumene et al. |
| 6,575,975 | B2 | 6/2003 | Brace et al. |
| 6,592,586 | B1 | 7/2003 | Michelson |
| 6,599,290 | B2 | 7/2003 | Bailey et al. |
| 6,602,256 | B1 | 8/2003 | Hayes |
| 6,602,257 | B1 | 8/2003 | Thramann |
| 6,605,090 | B1 | 8/2003 | Trieu et al. |
| 6,613,053 | B1 | 9/2003 | Collins et al. |
| 6,616,666 | B1 | 9/2003 | Michelson |
| 6,620,163 | B1 | 9/2003 | Michelson |
| 6,626,907 | B2 | 9/2003 | Blain et al. |
| 6,652,525 | B1 | 11/2003 | Assaker et al. |
| 6,669,700 | B1 | 12/2003 | Farris et al. |
| 6,676,703 | B2 | 1/2004 | Biscup |
| 6,679,883 | B2 | 1/2004 | Hawkes et al. |
| 6,699,249 | B2 | 3/2004 | Schlapfer et al. |
| 6,712,818 | B1 | 3/2004 | Michelson |
| 6,755,833 | B1 | 6/2004 | Paul et al. |
| 6,776,798 | B2 | 8/2004 | Camino et al. |
| 6,837,905 | B1 | 1/2005 | Lieberman |
| 6,890,334 | B2 | 5/2005 | Brace et al. |
| 6,916,320 | B2 | 7/2005 | Michelson |
| 6,926,737 | B2 | 8/2005 | Jackson |
| 6,936,050 | B2 | 8/2005 | Michelson |
| 6,936,051 | B2 | 8/2005 | Michelson |
| 6,964,664 | B2 | 11/2005 | Freid et al. |
| 6,969,390 | B2 | 11/2005 | Michelson |
| 7,001,387 | B2 | 2/2006 | Farris et al. |
| 7,033,394 | B2 | 4/2006 | Michelson |
| 7,041,105 | B2 | 5/2006 | Michelson |
| 7,041,135 | B2 | 5/2006 | Michelson |
| 7,044,952 | B2 | 5/2006 | Michelson |
| 7,048,739 | B2 | 5/2006 | Konieczynski et al. |
| 2002/0045898 | A1 | 4/2002 | Freid et al. |
| 2002/0058939 | A1 | 5/2002 | Wagner et al. |
| 2002/0120273 | A1 | 8/2002 | Needham et al. |
| 2002/0143400 | A1 | 10/2002 | Biscup |
| 2002/0173790 | A1 | 11/2002 | Chang et al. |
| 2002/0183755 | A1 | 12/2002 | Michelson |
| 2002/0183756 | A1 | 12/2002 | Michelson |
| 2002/0183757 | A1 | 12/2002 | Michelson |
| 2002/0188296 | A1 | 12/2002 | Michelson |
| 2003/0018335 | A1 | 1/2003 | Michelson |
| 2003/0023307 | A1 | 1/2003 | Michelson |
| 2003/0045880 | A1 | 3/2003 | Michelson |
| 2003/0060828 | A1 | 3/2003 | Michelson |
| 2003/0078668 | A1 | 4/2003 | Michelson |
| 2003/0105462 | A1 | 6/2003 | Haider |
| 2003/0181912 | A1 | 9/2003 | Michelson |
| 2003/0187443 | A1 | 10/2003 | Lauryssen et al. |
| 2003/0191471 | A1 | 10/2003 | Michelson |
| 2003/0191472 | A1 | 10/2003 | Michelson |
| 2003/0199876 | A1 | 10/2003 | Brace et al. |
| 2003/0199983 | A1 | 10/2003 | Michelson |
| 2003/0208204 | A1 | 11/2003 | Bailey et al. |
| 2003/0225409 | A1 | 12/2003 | Freid et al. |
| 2004/0019353 | A1 | 1/2004 | Freid et al. |
| 2004/0030338 | A1 | 2/2004 | Paul |
| 2004/0092939 | A1 | 5/2004 | Freid et al. |
| 2004/0097934 | A1 | 5/2004 | Farris et al. |
| 2004/0122426 | A1 | 6/2004 | Michelson |
| 2004/0127896 | A1 | 7/2004 | Lombardo et al. |
| 2004/0127897 | A1 | 7/2004 | Freid et al. |
| 2004/0127903 | A1 | 7/2004 | Schlapfer et al. |
| 2004/0127904 | A1 | 7/2004 | Konieczynski et al. |
| 2004/0133205 | A1 | 7/2004 | Thramann et al. |
| 2004/0181226 | A1 | 9/2004 | Michelson |
| 2004/0181229 | A1 | 9/2004 | Michelson |
| 2004/0186476 | A1 | 9/2004 | Michelson |

| | | | | | | |
|---|---|---|---|---|---|---|
| 2004/0193269 | A1 | 9/2004 | Fraser et al. | DE | 4409833 A1 | 10/1995 |
| 2004/0193270 | A1 | 9/2004 | DiMauro et al. | EP | 0179695 A1 | 4/1986 |
| 2004/0193271 | A1 | 9/2004 | Fraser et al. | EP | 0307241 A2 | 3/1989 |
| 2004/0210313 | A1 | 10/2004 | Michelson | EP | 1437105 A1 | 7/2004 |
| 2004/0230309 | A1 | 11/2004 | DiMauro et al. | GB | 0401362.9 | 2/2004 |
| 2005/0038513 | A1 | 2/2005 | Michelson | WO | 89/09035 A1 | 10/1989 |
| 2006/0241616 | A1 | 10/2006 | Konieczynski et al. | WO | 97/20526 A1 | 6/1997 |
| 2007/0073297 | A1 | 3/2007 | Reynolds | WO | 99/63914 A1 | 12/1999 |
| 2008/0097444 | A1 | 4/2008 | Erickson et al. | WO | 00/66044 A1 | 11/2000 |

FOREIGN PATENT DOCUMENTS

| | | | |
|---|---|---|---|
| CA | 2133276 | | 4/1995 |
| CA | 2163243 | A1 | 9/1995 |
| CA | 2383634 | A1 | 8/2001 |

| | | |
|---|---|---|
| WO | 00/66045 A1 | 11/2000 |
| WO | 2007035582 A2 | 3/2007 |
| WO | 2008021656 A2 | 2/2008 |

* cited by examiner

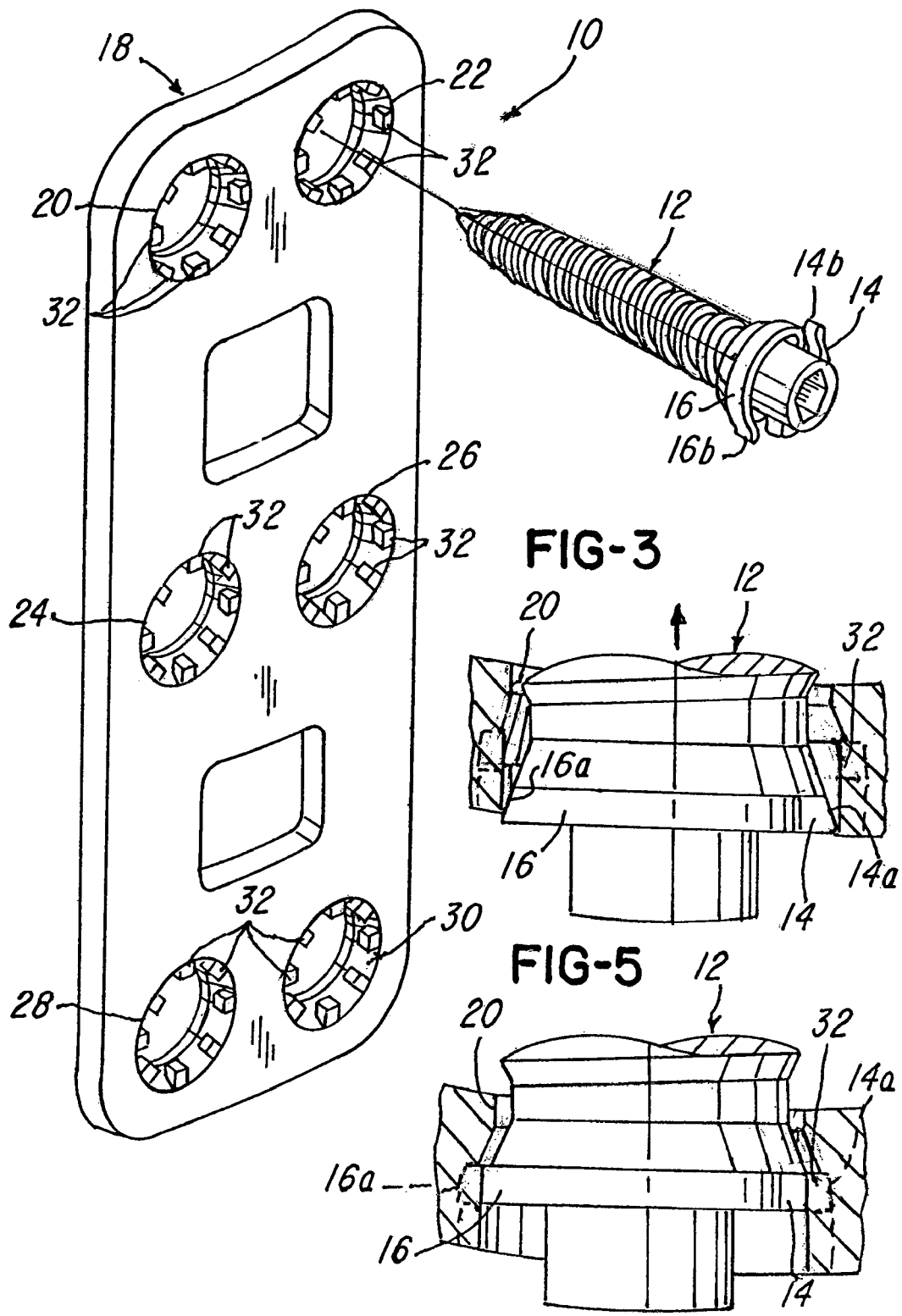

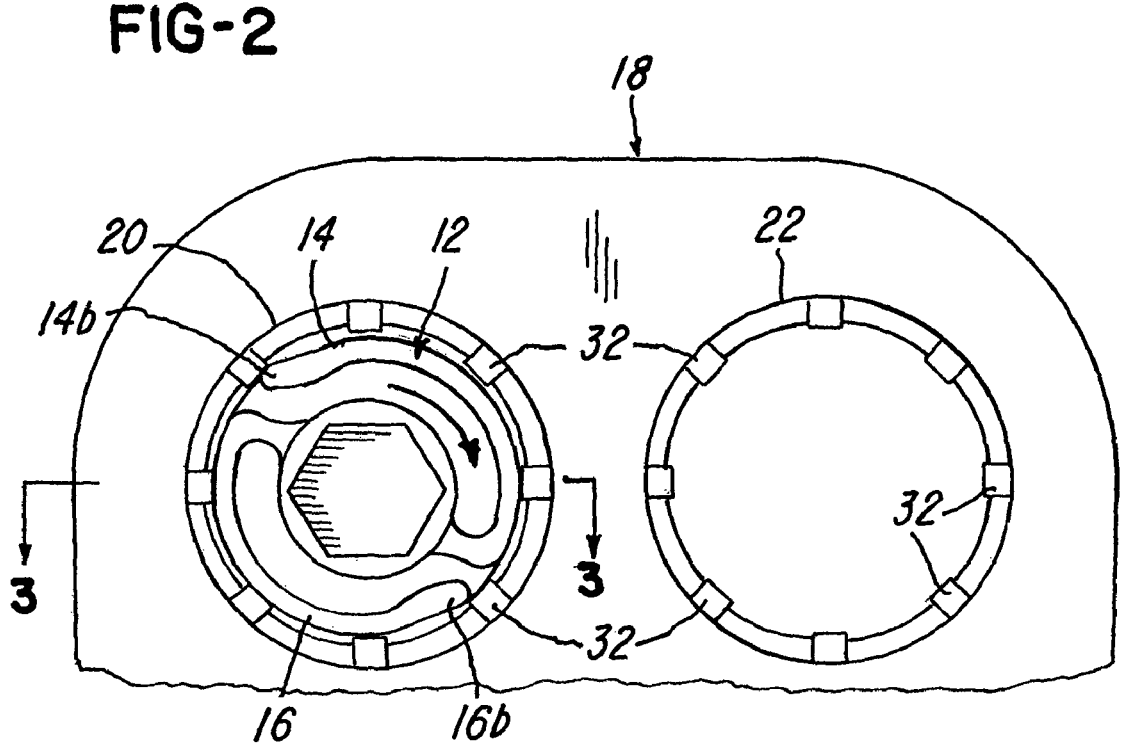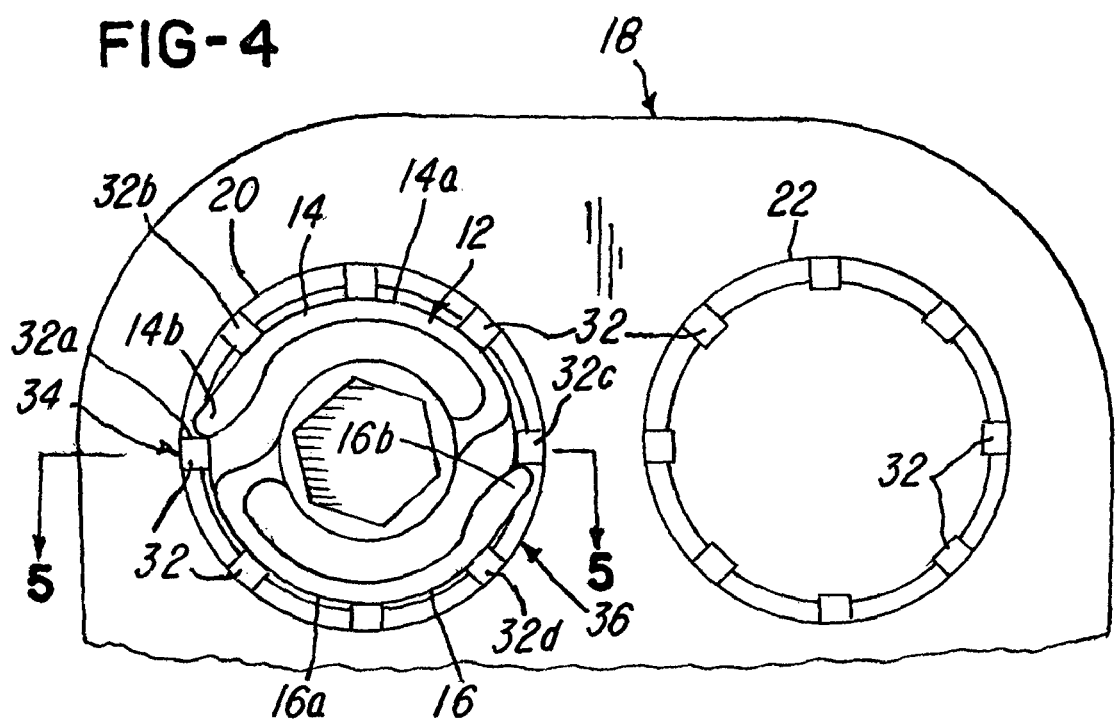

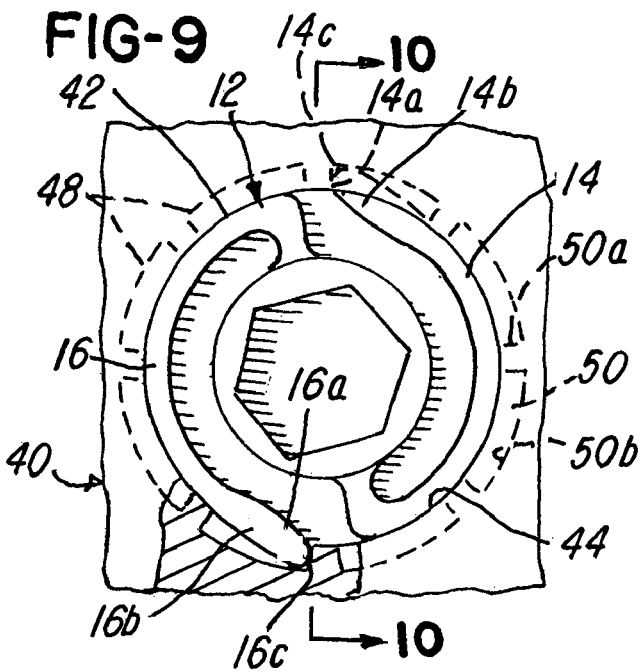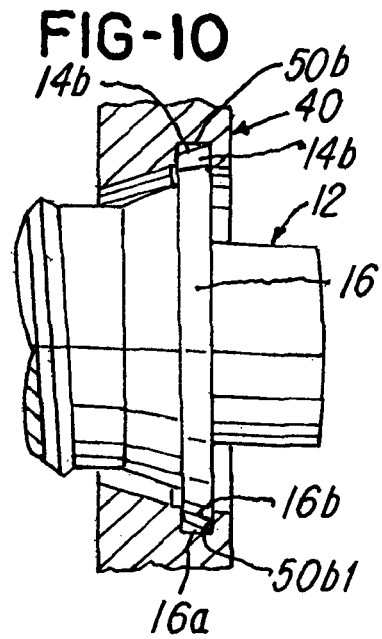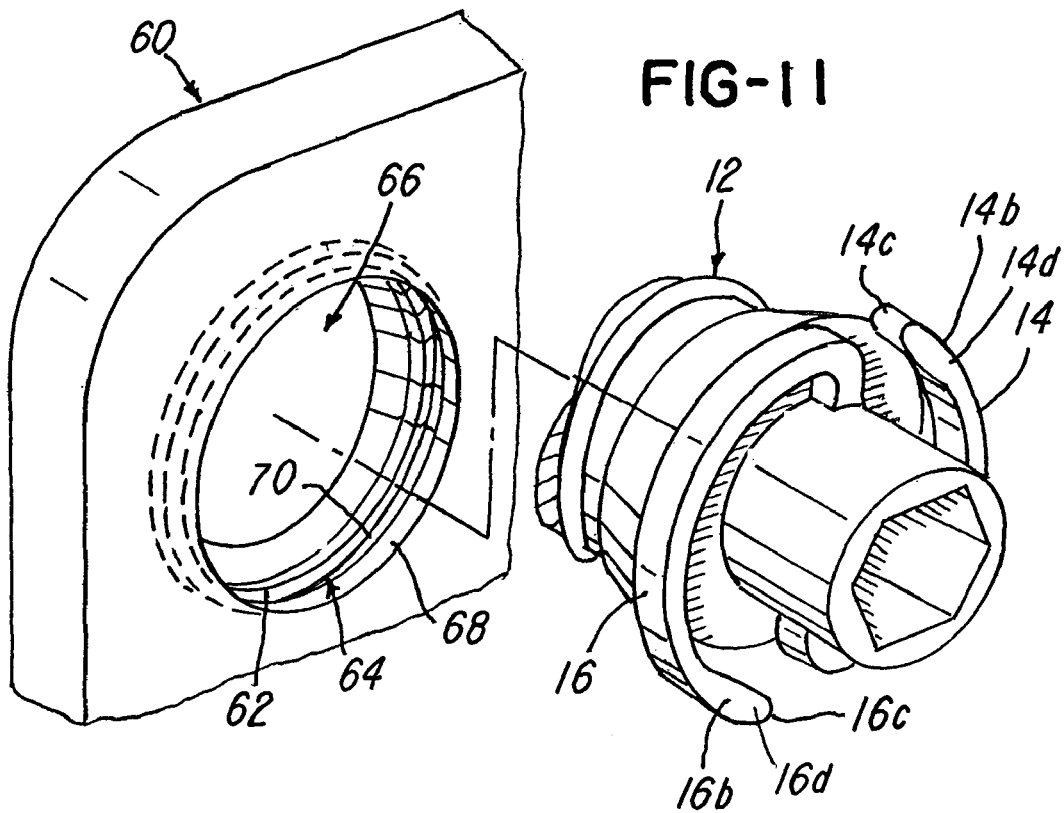

US 7,963,982 B2

IMPLANT PLATE SCREW LOCKING SYSTEM AND SCREW HAVING A LOCKING MEMBER

BACKGROUND OF THE INVENTION

1. Field of the Invention

This invention relates to a implant plate system, device and locking screw having at least one locking member. The preferred application for the device is in spinal surgery, however, applications in other areas of orthopedic surgery are appropriate.

2. Description of the Related Art

Many types of prosthetic devices have been proposed in the past. For example, U.S. Pat. No. 5,192,327 to Brantigan concerns a surgical prosthetic modular implant used singularly or stacked together to support and fuse together adjacent vertebrae or to totally or partially replace one or more vertebrae in a vertebral column. Other surgical implant devices and methods are shown in U.S. Pat. Nos. 4,488,543; 5,192,327; 5,261,911; 5,549,612; 5,713,899; 5,776,196; 6,136,002; 6,159,245; 6,224,602; 6,258,089; 6,261,586; 6,264,655; 6,306,136; 6,328,738; 6,361,537 and 6,592,586. Some or all of these devices have improved the success rate and have simplified the surgical techniques in inter-body veritable fusion.

U.S. Pat. No. 6,258,089 B1 issued Jul. 10, 2001 to Campbell et al. for an Anterior Cervical Plate And Fixation System discloses an anterior cervical plate is disclosed, along with threaded fasteners for securing the plate to vertebrae or other osseous material. The cervical plate has several pockets or apertures, preferably at least four, to receive a corresponding number of the fasteners. The pockets have spherical surfaces, and the fasteners have heads with similarly sized spherical surfaces, which when engaged permit each of the fasteners to be oriented at a variety of projection angles with respect to the plate. In connection with each pocket, the cervical plate incorporates a fastener retaining feature. The feature can take the form of a cantilevered tab or a beam supported at its opposite ends, in each case plastically deformable between an open position for admitting the fastener and a closed position for preventing retraction.

U.S. Pat. No. 5,549,612 issued Aug. 27, 1996 to Yapp et al. for Osteosynthesis Plate System discloses an osteosynthesis plate system is particularly well adapted to securely fuse adjacent cervical vertebrae. The plates are adapted for mounting upon the anterior or posterior surfaces of the vertebrae. Plates for mounting on the anterior vertebral surfaces have a concave bone contacting surface and a bone screw locking mechanism integral with each screw hole. Moreover, the bone contacting surface of the plate has a plurality of bone penetrating protrusions to more securely affix the plate to bone. Plates for mounting on the posterior vertebral surfaces also have bone penetrating protections on their bone contacting surfaces. Such plates are formed so as to have a curved bone contacting surface that is concave in the transverse axis of the plate and convex in the longitudinal axis of the plate. The screw holes of such plates are constructed so as to guide a bone screw along a desired angle to improve the anchoring of the screws in bone.

U.S. Pat. No. 4,488,543 issued Dec. 18, 1984 to Tornier for Device For Osteosynthesis Of Fractures Of The Extremities Of The Femur discloses a device for osteosynthesis of the fractures of the extremities of the femur comprises a plate in which holes are provided for the passage of screws intended to be inserted into the bone to make the fractured bone and the plate solid. One end of the plate to be applied against one of extremities of the femur is wider than the other end and includes three holes arranged in an isosceles triangle. The median plane of the one end defines a plane which forms, with the plane of the rest of the plate, an obtuse angle of between 160° and 175°.

U.S. Pat. No. 6,361,537 B1 issued Mar. 26, 2002 to Anderson for Surgical Plate With Pawl And Process For Repair Of A Broken Bone discloses a surgical plate and process for preventing screw backout of repaired bones. At least one pawl is provided on a surgical plate adjacent to a screw hole. A screw having a ratchet wheel is inserted through the hole and screwed into the bone. The pawl engages the ratchet wheel to prevent rotational movement of the screw to prevent the screw from backing out. In a preferred embodiment, a pawl plate Comprising a base portion is rigidly connected to the surgical plate and a torsion bar is pivotally connected to the base portion. The pawl is positioned at the end of the torsion bar. In the preferred embodiments, several of these special screw holes with pawls, and several screws (each with a ratchet wheel) are used in bone repair.

While the above approaches may have yielded favorable results in certain circumstances, there remains a need for reducing the need for multiple parts or tools and for providing a simpler, more reliable means and system of facilitating prevention of the screws from migrating out of the bone by axial or rotational movement after the plate is fixed thereto.

Among some of the problems associated with the prior art devices is that after the device is inserted into a patient during a surgical procedure, there was a possibility of inadequate fixation of the implant device due to false-locking of fixating screws.

Another problem with the prior art devices is that the implant device and associated bone graft could loosen after the surgical procedure due to undesired back-out of fixating screws.

Moreover, in some of the prior art devices, the fixation screws are locked to the prosthetic device in a multiple-step process, increasing the possibility for user error or false fixation.

Another problem with prior art implant plate systems is that the screws or fasteners which secured the plate had a tendency to withdraw, causing injury to local structures by the screws themselves.

What is needed, therefore, is a system and method, which facilitates overcoming one or more of the aforementioned problems as well as other problems and to provide a device that has unique features that will facilitate reducing the risk associated with neurological surgeries and advance the present state of the art.

Therefore, there is a need for a plate and fixation system in which bone screws or other fasteners are more securely retained and less likely to work loose or migrate, which reduces or eliminates the need for auxiliary components, screws, tools or additional fixtures.

SUMMARY OF THE INVENTION

It is, therefore, one object of the embodiments to provide a plate having an improved locking system which in one illustrative embodiment comprises a screw having a member, such as a resilient pawl, that is received in a channel in the plate to facilitate preventing screw migration.

In one aspect this invention comprises a plate system comprising a screw having a screw head, a plate having an aperture for receiving the screw, and the screw comprising at least one pawl for restricting or preventing the screw from moving in at least one of an axial direction or a rotational direction.

In another aspect this invention comprises a locking screw for use in a plate, comprising a threaded portion, a screw head, and the screw head comprising at least one member for cooperating with the plate to prevent migration or movement of the screw head.

These and other objects and advantages of the invention will be apparent from the following description, the accompanying drawings and the appended claims.

BRIEF DESCRIPTION OF THE DRAWINGS

FIG. 1 is a perspective view illustrating one embodiment of the invention where at least one or a plurality of pawls are embodied in the screw;

FIGS. 2-5 are various fragmentary views illustrating various details of the embodiment shown in FIG. 1;

FIGS. 7-10 are various fragmentary and sectional views showing various details of the embodiment shown in FIG. 6;

FIG. 11 is a fragmentary perspective view illustrating another embodiment of the invention with a continuous channel in a plate;

DETAILED DESCRIPTION OF PREFERRED EMBODIMENTS

Figure 6:
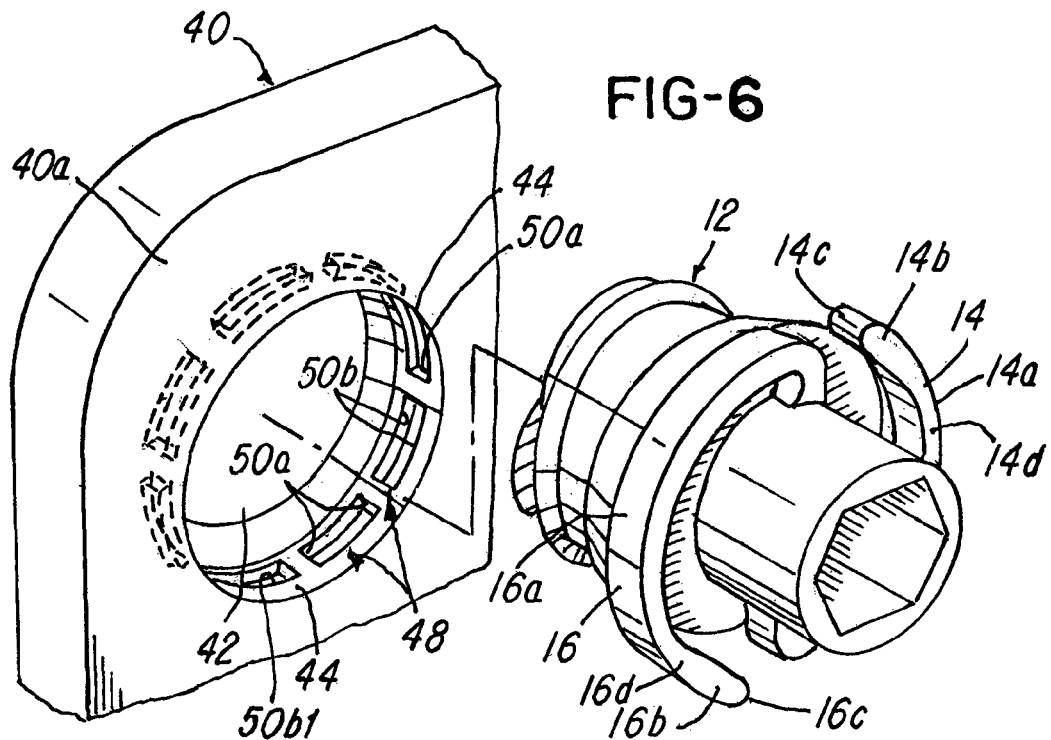
FIG. 6 is a perspective and fragmentary view of another embodiment of the invention showing various notched-out areas in the plate.
Figure 7:
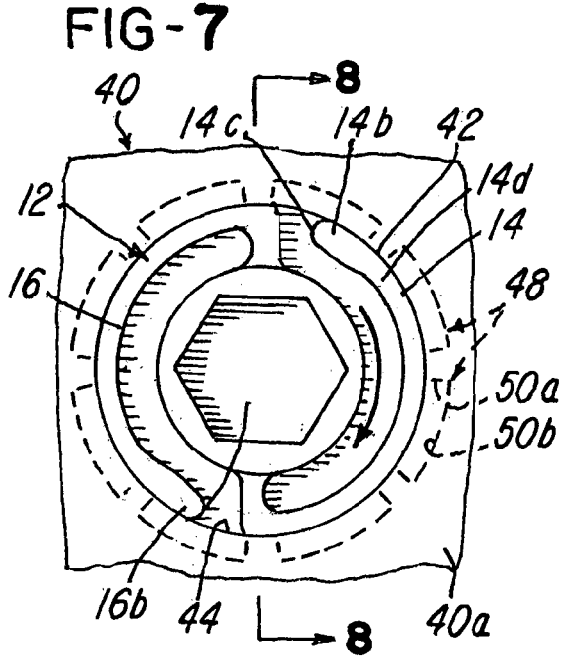

Referring now to FIGS. 1-17, means and apparatus for preventing axial and/or rotational movement in the form of a resilient lock may be provided. FIGS. 1-17 illustrate a system and method for providing an integral lock. In FIG. 1, a system 10 comprises a screw 12 comprises at least one or a plurality of resilient fingers, springs, pawls, elastic projections or members 14 and 16. The fingers or members are resilient, elastic and deflectable as with prior embodiments. In the illustration being described, the fingers or members 14 and 16 are integrally formed in the screw 12, but they could be non-integral or assembled from multiple parts.

Notice in the embodiment illustrated in FIGS. 1-5 that a plate 18 is provided having a plurality of apertures 20, 22, 24, 26, 28 and 30. In this embodiment, the plate 18 comprises a plurality of notches, projections or stops 32 associated with each aperture. The members 14 and 16 are normally biased a predetermined distance away from the axis of the screw 12 so that when the screw 12 is received in an aperture, such as aperture 20, the screw 12 becomes locked or retained in the plate 18.

Notice in FIG. 3 that the pawls 14 and 16 comprise beveled, curved or angled surfaces 14a and 16a which engage the notches 32a, 32b and 32c, 32d, respectively, and deflected inwardly (as viewed in FIG. 2) toward an axis of the screw 12 as the screw 12 is screwed into bone. After the screw 12 is screwed into the bone to a desired depth, an end 14b (FIG. 1) of finger 14 and an end 16b of finger 16 becomes received between adjacent notches 32, such as in areas 34 and 36 (FIG. 4), between adjacent notches 32. Notice that a surface 32a (FIG. 4) of at least one notch 32 engages end 14b of the resilient pawl 14, which prevents rotational movement in a counterclockwise direction (as viewed in FIG. 4). At this point, ends 14b and 16b of fingers or pawls 14 and 16, respectively, are received in the areas 34 and 36 as illustrated in FIG. 4.

Thus, in the embodiment being illustrated, FIGS. 1-5, the pawls 14 and 16 cooperate with the notches or projections 32 to prevent rotational movement of the screw 12 after it is received in the plate 18 and in the bone.

FIGS. 6-10 and 16 illustrate another embodiment wherein both axial and rotational movement of the screw 12 is prevented or restricted. In this embodiment, a plate 40, which is shown only in fragmentary view for ease of illustration and description, is provided with at least one or a plurality of screw-receiving apertures 42, as best described in FIG. 6. In this regard, the plate 40 comprises a wall 44 defining the screw-receiving aperture 42. The wall 44 also comprises a plurality of notched-out areas 48 associated with aperture 42. Each of the plurality of notched-out areas 48 is defined by a wall 50 having side or wall surfaces 50a and inner surfaces 50b that cooperate to define the notched out area 48.

Figure 8:
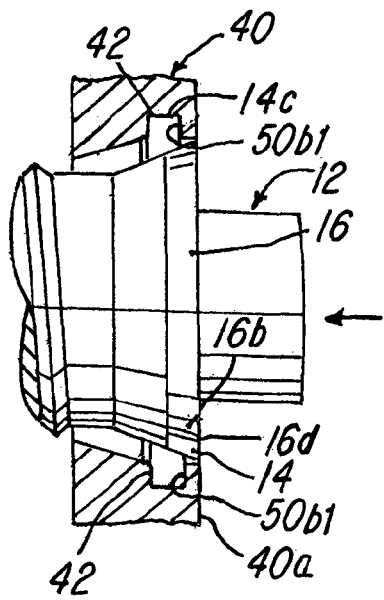

As illustrated in FIGS. 8 and 10, the pawls or fingers 14 and 16 may comprise beveled or angled camming surfaces 14a and 16a, respectively, that resiliently deflect inwardly toward the axis of screw 12 after the screw 12 is received in the aperture defined by wall 52 and screwed into the bone. In the embodiment illustrated in FIGS. 6-10, the surfaces 14a and 16a engage the surface or edge 44 (FIG. 6) of the plate 40 and yield inwardly (as viewed in FIGS. 7-8) toward the axis of the screw 12. After the surface 14b of pawl 14 and surface 16b of pawl 16 clear the surface 50b1 (FIG. 8), the ends 14c and 16c of resilient pawls 14 and 16 move outwardly or away from the axis of the screw 12 until at least a portion, such as ends 14c and 16c, are received in one of the notched-out areas 48, whereupon the surfaces 14d and 16d (FIG. 6) become operatively related to and generally opposed to the surface 50b1, as illustrated in FIGS. 9-10.

Notice that when the pawls 14 and 16 are in the locked position, the screw 12 is prevented or restricted from moving, migrating or withdrawing axially (i.e., to the right as viewed in FIG. 10). Notice also that the walls 50a of notched-out areas 48 cooperate with ends 14c and 16c to restrict or prevent rotational movement of the screw 12 in a counter-clockwise direction in the illustration being described.

Figure 12:
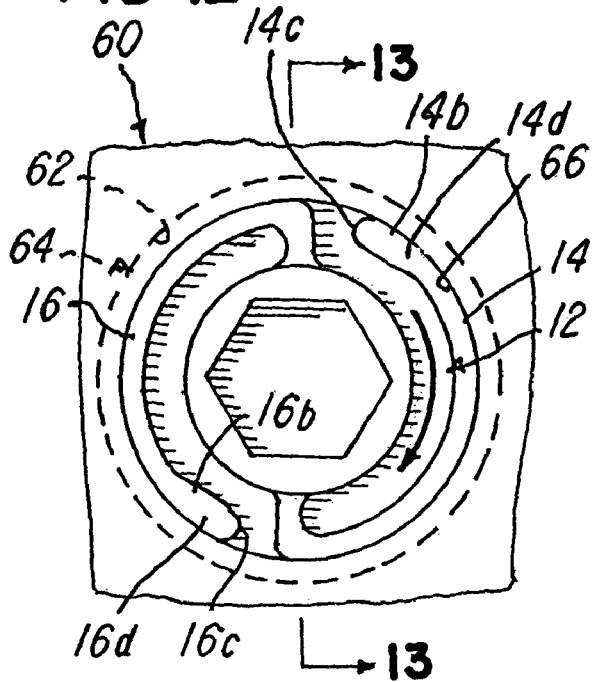
FIGS. 12-15 are various fragmentary and sectional views illustrating various details of the embodiments shown in FIGS. 11.
Figure 13:
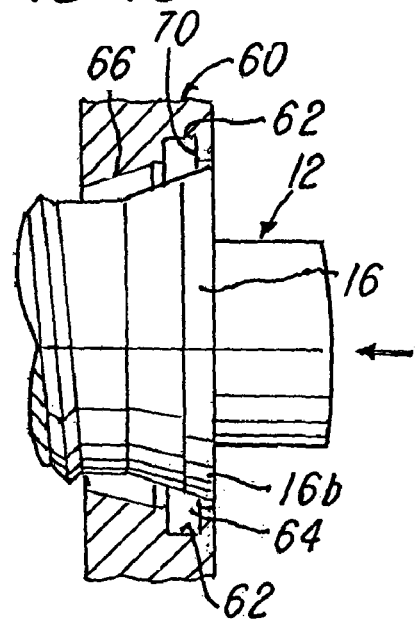
Figure 14:
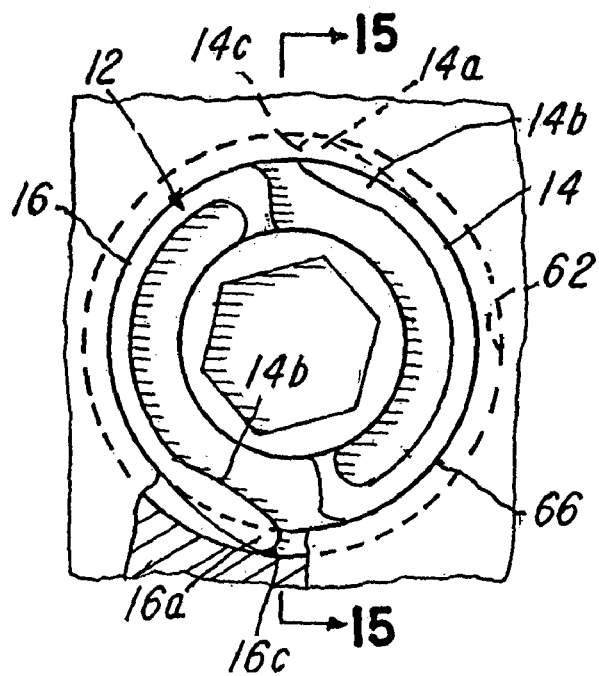
Figure 15:
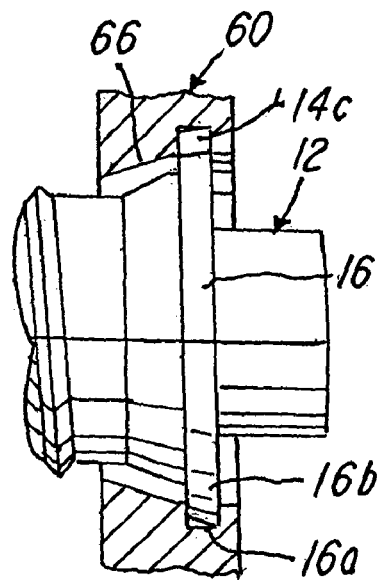

FIGS. 11-15 and 17 show a similar arrangement except that a plate 60 comprises a U-shaped wall or surface 62 that defines a single, continuous notched-out area, endless channel, or channel 64. In this embodiment, at least a portion of the ends 14c and 16c are received in the channel or notched-out area 64, as shown in FIGS. 14-15. As with the embodiment described relative to FIGS. 6-10 and 16, this embodiment also prevents axial movement of the screw 12.

After screw 12 is received in an aperture, such as aperture 66 (FIG. 11) of plate 60, as best seen in FIG. 11, the angled surfaces 14a and 16a engage or cam against the surface 68 (FIG. 11) and are deflected inwardly, as illustrated in FIGS. 12-13. The screw 12 is driven until the surfaces 14a and 16a clear the wall or surface 70 (FIG. 11), whereupon at least a portion of the fingers, such as ends 14c and 16c, spring or move away from the screw axis end and are received in the channel 64, whereupon the surfaces 14d (FIG. 12) and 16d become generally opposed to surface 70 (FIG. 13). This prevents or restricts axial movement or withdrawal of the screw 12 from the bone and plate 60.

Figure 16:
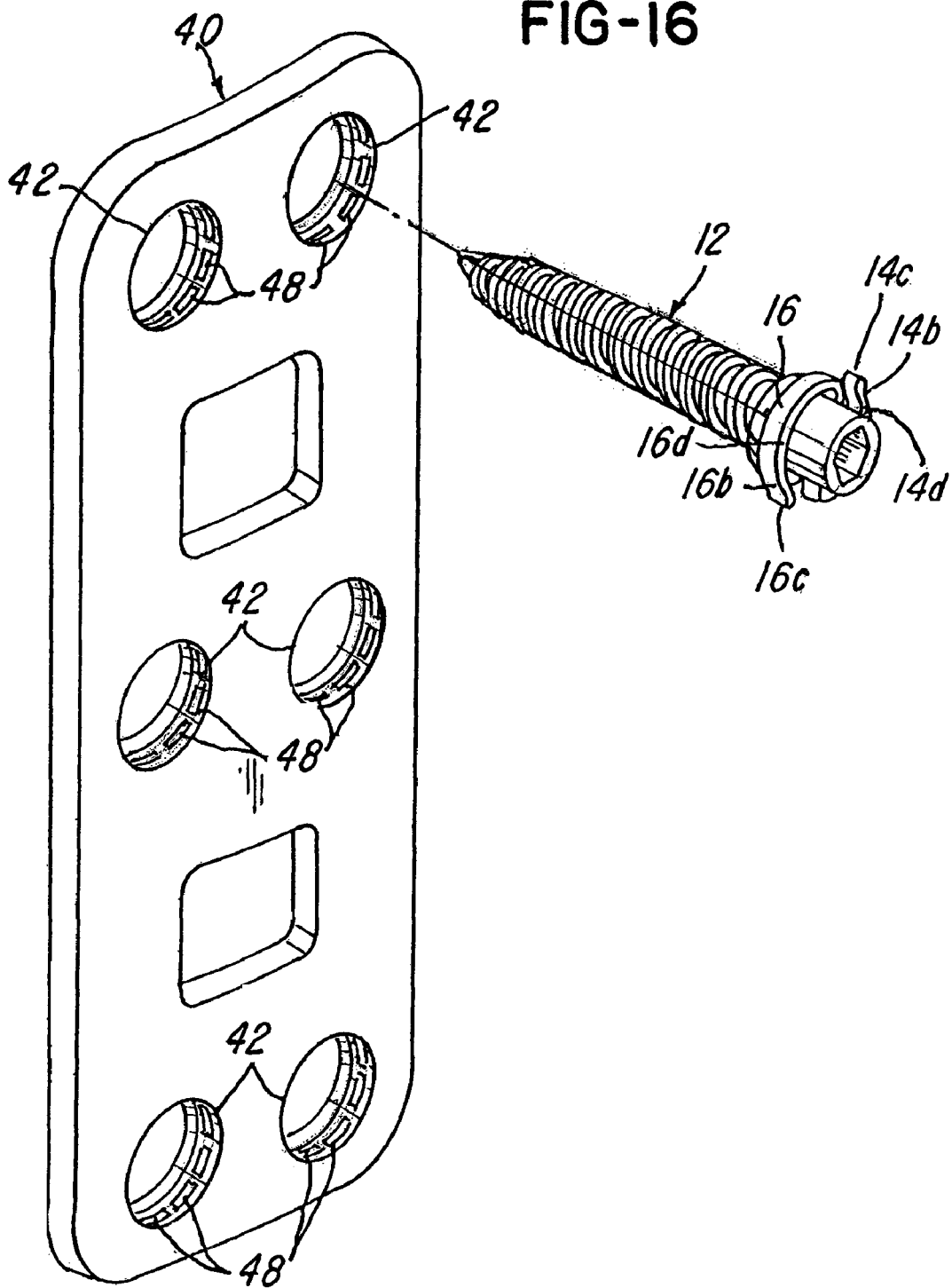
FIG. 16 is a perspective view showing the screw and plate according to the embodiment illustrated in FIGS. 6-10.
Figure 17:
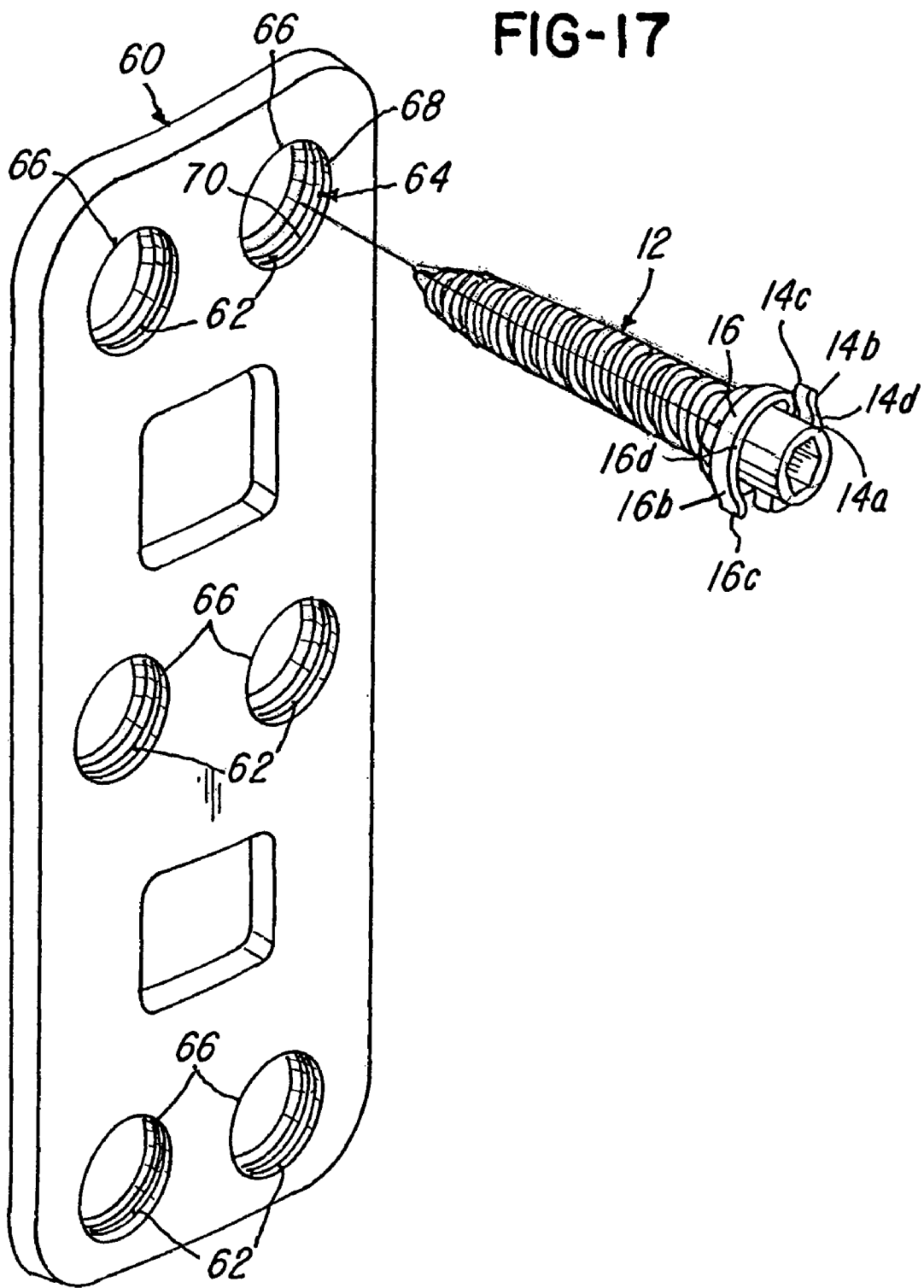
FIG. 17 is a perspective view of the embodiment corresponding to the embodiments shown in FIGS. 11-15.

FIGS. 16 and 17 are perspective views of the entire plate and screws for the embodiments shown in FIGS. 6-10 and 11-15, respectively. Of course, the various pawls, fingers, notched-out areas, notches and the like described could be adapted to have other shapes or configurations, with more or fewer of them, for example, without departing from the desire to provide a locking system and method that provides means for restricting axial and rotational movement of a screw in a plate.

Advantageously, various embodiments described relative to FIGS. 1-17 provide various means, apparatus and methods for preventing axial and/or rotational movement of the screw and for providing an integral lock to facilitate retaining the screw in a bone, such as a spinal bone. The system and method according to these embodiments show various means for providing a lock for retaining the screw in the plate in which it is received.

Advantageously, the system and method provide means and apparatus for locking a screw to a plate and preventing withdrawal of the screw or unscrewing of the screw. The illustrative embodiments provide means and apparatus for facilitating preventing rotational movement of at least one or a plurality of screws in at least one or a plurality of directions and axial movement of the at least one or a plurality of screws.

While the apparatus and method described constitute preferred embodiments of this invention, it is to be understood that the invention is not limited to this precise apparatus and method, and that changes may be made in either without departing from the scope of the invention, which is defined in the appended claims.

What is claimed is:

1. A plate system comprising:
   a screw having a screw head;
   a plate having an aperture for receiving said screw; and
   said screw comprising at least one member for restricting or preventing said screw from moving in at least one of an axial direction or a rotational direction;
   wherein said at least one member comprises an elastic or resilient pawl having an end that is integral with said screw head and a generally arcuate or curved portion;
   wherein said plate comprises a wall that defines said aperture, said wall being adapted to define at least one receiving area for receiving at least a portion of said pawl and for restricting or preventing said screw from moving in at least one of said axial direction or said rotational direction wherein said at least one member is normally biased away from an axis of said screw; wherein said pawl comprises a beveled or angled surface; wherein said beveled or angled surface tapers inwardly towards said axis as said beveled or angled surface extends from said screw head towards a threaded portion of said screw; and wherein said beveled or angled surface deflects inwardly toward said axis as said screw is screwed into bone or after said screw is received in said aperture.

2. The plate system as recited in claim 1 wherein said plate comprises a ratchet associated with said aperture, said ratchet cooperating with and being engaged by said at least one member to retain said screw in said plate.

3. The plate system as recited in claim 1 wherein said at least one member prevents movement of said screw in both axial and rotational directions.

4. The plate system as recited in claim 1 wherein said plate comprises a wall that defines said aperture, said wall being adapted to define at least one receiving area for receiving at least a portion of said at least one member and for restricting or preventing said screw from moving in said at least one of said axial direction or said rotational direction.

5. The plate system as recited in claim 1 wherein said at least one member comprises a plurality of pawls and said plate being adapted to define at least one notched-out area or receiving area for receiving at least a portion of each of said plurality of pawls.

6. The plate system as recited in claim 1 wherein said plate comprises a wall having a plurality of detents associated therewith for cooperating with said at least one member to restrict or prevent rotational movement of said screw.

7. The plate system as recited in claim 1 wherein said plate comprises a plurality of walls that define a plurality of screw-receiving apertures for receiving a plurality of screws, respectively, each of said plurality of screws having said at least one member integrally formed on said screw head.

8. The plate system as recited in claim 7 wherein each of said at least one member is resilient, each of said plurality of walls being adapted to define at least one notched-out or receiving area for receiving an end of said at least one member in order to restrict or prevent said screw from moving in each of said axial direction or said rotational direction.

9. The plate system as recited in claim 1 wherein said at least one member comprises a plurality of pawls.

10. The plate system as recited in claim 9 wherein said plurality of pawls are integral with said screw head.

11. The plate system as recited in claim 9 wherein each of said plurality of pawls are resilient or elastic.

12. The plate system as recited in claim 1 wherein said screw comprises a plurality of pawls that are generally curved or arcuate.

13. The plate system as recited in claim 12 wherein said plurality of pawls are resilient or elastic, each of said plurality of pawls comprising an end that is normally biased away from an axis of said screw.

14. The plate system as recited in claim 1 wherein said plate comprises a plurality of apertures defined by a plurality of surfaces, said plurality of surfaces defining at least one channel for receiving said at least one member, thereby preventing said screw from moving in at least one of an axial direction or a rotational direction.

15. The plate system as recited in claim 13 wherein said screw is prevented from moving in both said axial direction and said rotational direction.

16. The plate system as recited in claim 14 wherein said at least one channel is an endless channel associated with said aperture for receiving at least a portion of said at least one member.

17. A locking screw system for use with an implant plate, comprising:
   a threaded portion;
   a screw head; and
   said screw head comprising at least one member for cooperating with said plate to facilitate preventing migration or movement of said screw head;
   wherein said at least one member comprises an elastic or resilient pawl having an end that is integral with said screw head and a generally arcuate or curved portion;
   wherein said plate comprises a wall that defines an aperture, said wall being adapted to define at least one receiving area for receiving at least a portion of said pawl and for restricting or preventing said screw from moving in at least one of an axial direction or a rotational direction wherein said at least one member is normally biased away from an axis of said screw; wherein said pawl comprises a beveled or angled surface; wherein said beveled or angled surface tapers inwardly towards said axis as said beveled or angled surface extends from said screw head towards a threaded portion of said screw; and wherein said beveled or angled surface deflects inwardly toward said axis as said screw is screwed into bone or after said screw is received in said aperture.

18. The locking screw system as recited in claim 17 wherein said at least one member is a resilient pawl.

19. The locking screw system as recited in claim 18 wherein said resilient pawl is integral with said screw head.

20. The locking screw system as recited in claim 19 wherein said resilient pawl is arcuate or curved.

21. The locking screw system as recited in claim 17 wherein said at least one member has an end and a curved portion joining said end to said screw, said at least one member being resilient and causing said end to be normally biased away from an axis of said screw a predetermined distance so that when said screw is received in said plate, said screw migration or movement is prevented.

22. The locking screw system as recited in claim 17 wherein said screw head comprises a plurality of resilient pawls.

23. The locking screw system as recited in claim 17 wherein said migration or movement is at least one of axial movement or rotational movement of said threaded portion.

24. The locking screw system as recited in claim 17 wherein said migration or movement is axial movement.

25. The locking screw system as recited in claim 17 wherein said migration or movement is rotational movement.

* * * * *